United States Patent
Egley et al.

(10) Patent No.: US 10,960,124 B2
(45) Date of Patent: Mar. 30, 2021

(54) DEVICES, SYSTEMS, AND METHODS FOR HEATING DIALYSATE FOR DIALYSIS MACHINES

(71) Applicant: Fresenius Medical Care Holdings, Inc., Waltham, MA (US)

(72) Inventors: Bert D. Egley, Walnut Creek, CA (US); Daniel H. Schmidt, Petaluma, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 356 days.

(21) Appl. No.: 16/029,374

(22) Filed: Jul. 6, 2018

(65) Prior Publication Data
US 2020/0009310 A1    Jan. 9, 2020

(51) Int. Cl.
  *A61M 1/28*    (2006.01)
(52) U.S. Cl.
  CPC ....... *A61M 1/287* (2013.01); *A61M 2205/128* (2013.01); *A61M 2205/3331* (2013.01); *A61M 2205/3334* (2013.01); *A61M 2205/3368* (2013.01); *A61M 2205/3379* (2013.01); *A61M 2205/3584* (2013.01); *A61M 2205/362* (2013.01); *A61M 2205/3606* (2013.01); *A61M 2205/505* (2013.01); *A61M 2205/581* (2013.01); *A61M 2209/084* (2013.01)
(58) Field of Classification Search
  CPC .. A61M 1/14; A61M 1/166; A61M 2205/127; A61M 2209/084; A61M 2205/36; A61M 2205/3633; A61M 2205/3666; A61B 50/10; A61B 50/13
See application file for complete search history.

(56) References Cited

U.S. PATENT DOCUMENTS

| 3,868,154 A | 2/1975 | MacDonald et al. |
| 4,052,589 A * | 10/1977 | Wyatt ............... A47J 39/006 219/400 |

(Continued)

FOREIGN PATENT DOCUMENTS

| WO | 0057928 A1 | 10/2000 |
| WO | 15013761 A1 | 2/2015 |

OTHER PUBLICATIONS

International Search Report and Written Opinion for International Application No. PCT/US2019/040447, dated Oct. 2, 2019, 12 pages.

*Primary Examiner* — Laura A Bouchelle
(74) *Attorney, Agent, or Firm* — Kacvinsky Daisak Bluni, PLLC

(57) ABSTRACT

Dialysis machines and methods for heating dialysate before delivery into a dialysis patient (e.g., peritoneal dialysis machines) may comprise a dialysis machine including one or more internal cooling components configured to expel heated air from the dialysis machine. A receptacle may be configured to receive one or more containers of dialysate. The one or more containers of dialysate may be positionable relative to the expelled heated air of the dialysis machine. The expelled heated air may be flowable around the one or more containers of dialysate to increase a temperature of the dialysate. The receptacle may include a stand for positioning the dialysis machine such that the expelled heated air is directed around the one or more containers of dialysate.

14 Claims, 8 Drawing Sheets

(56) References Cited

U.S. PATENT DOCUMENTS

| | | | |
|---|---|---|---|
| 4,628,186 A | 12/1986 | Bergemann et al. | |
| 6,284,139 B1 | 9/2001 | Piccirillo | |
| 6,595,948 B2 | 7/2003 | Suzuki et al. | |
| 6,869,538 B2 | 3/2005 | Yu et al. | |
| 7,031,602 B2 | 4/2006 | Faries, Jr. et al. | |
| 7,153,285 B2 | 12/2006 | Lauman et al. | |
| 7,326,882 B2 | 2/2008 | Faries, Jr. et al. | |
| 7,736,328 B2 * | 6/2010 | Childers | A61M 1/282 604/29 |
| 8,226,293 B2 | 7/2012 | Faries, Jr. et al. | |
| 8,226,605 B2 | 7/2012 | Faries, Jr. et al. | |
| 8,597,505 B2 * | 12/2013 | Fulkerson | A61M 1/3672 210/86 |
| 8,692,167 B2 | 4/2014 | Hedmann et al. | |
| 9,211,381 B2 | 12/2015 | Faries et al. | |
| 9,265,873 B2 | 2/2016 | Ritter | |
| 9,555,181 B2 | 1/2017 | Hedmann et al. | |
| 9,656,029 B2 | 5/2017 | Tsang et al. | |
| 2003/0133265 A1 | 7/2003 | Kinsey et al. | |
| 2004/0138607 A1 | 7/2004 | Burbank et al. | |
| 2004/0215129 A1 | 10/2004 | Edgson et al. | |
| 2013/0136431 A1 * | 5/2013 | Peters | F25B 21/04 392/308 |
| 2016/0175552 A1 | 6/2016 | Harrington | |
| 2017/0027541 A1 * | 2/2017 | Henderson | A61B 8/4427 |
| 2018/0093031 A1 | 4/2018 | Crawford et al. | |
| 2018/0140764 A1 | 5/2018 | Georg et al. | |

* cited by examiner

DEVICES, SYSTEMS, AND METHODS FOR HEATING DIALYSATE FOR DIALYSIS MACHINES

FIELD OF THE DISCLOSURE

The disclosure generally relates to dialysis machines, and more particularly to devices, systems, and methods for heating dialysate for dialysis machines.

BACKGROUND OF THE INVENTION

Dialysis machines are known for use in the treatment of renal disease. The two principal dialysis methods are hemodialysis (HD) and peritoneal dialysis (PD). During hemodialysis, the patient's blood is passed through a dialyzer of a hemodialysis machine while also passing dialysate through the dialyzer. A semi-permeable membrane in the dialyzer separates the blood from the dialysate within the dialyzer and allows diffusion and osmosis exchanges to take place between the dialysate and the blood stream. During peritoneal dialysis, the patient's peritoneal cavity is periodically infused with dialysate or dialysis solution. The membranous lining of the patient's peritoneum acts as a natural semi-permeable membrane that allows diffusion and osmosis exchanges to take place between the solution and the blood stream. Automated peritoneal dialysis machines, called PD cyclers, are designed to control the entire peritoneal dialysis process so that it can be performed at home, usually overnight, without clinical staff in attendance.

A dialysis machine, such as a peritoneal dialysis machine, may include one or more containers (e.g., bags) containing a fluid, e.g., a dialysate for patient infusion. In peritoneal dialysis machines, for example, tubing as one or more fluid lines are inserted into an abdomen of a patient for flowing fresh dialysate and removing used dialysate, waste, and excess fluid. Fresh dialysate may be heated from room temperature, e.g., approximately 65° F. to 75° F. (18° C. to 24° C.) to body temperature, e.g., approximately 98° F. to 99° F. (36° C. to 37° C.), prior to flowing into the patient. One challenge in heating multiple bags of dialysate is that a significant amount of power may be needed for each dialysis treatment cycle. Large power requirements may be difficult to supply in some geographical areas, e.g., developing countries, field operations, and/or rural locations. Conserving energy overall in the operation of a dialysis system may also allow total power consumption to be optimized and may allow for other efficiencies to be realized in the dialysis treatment, e.g., reduction in treatment time, to the benefit of the patient.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

An exemplary embodiment of a system for heating dialysate before delivery into a patient in accordance with the present disclosure may comprise a dialysis machine including one or more internal cooling components configured to expel heated air from the dialysis machine. A receptacle may be configured to receive one or more containers of dialysate, and the one or more containers of dialysate may be positionable relative to the expelled heated air of the dialysis machine. The expelled heated air may be flowable around the one or more containers of dialysate to increase a temperature of the dialysate.

According to various of the foregoing and other embodiments of the present disclosure, the receptacle may include a stand for positioning the dialysis machine such that the expelled heated air may be directed around the one or more containers of dialysate. The stand may position the dialysis machine vertically over a section for receiving the one or more containers of dialysate, and the stand may include one or more vents. The one or more vents may include baffles for directing the expelled heated air around the one or more containers of dialysate. The receptacle may be a movable cart. The one or more containers of dialysate may be stackable in the first section of the receptacle. The first section may be insulated for minimizing heat transfer from the one or more containers of dialysate to ambient air. The one or more internal cooling components may include a fan. During operation, the dialysis machine may generate internal heat resulting in heated air, wherein the fan may be configured to simultaneously cool the dialysis machine and heat the one or more containers of dialysate by expelling the heated air from the dialysis machine and directing the expelled heated air to flow around the one or more containers of dialysate.

An exemplary embodiment of a method for heating dialysate before delivery into a dialysis patient in accordance with the present disclosure may comprise operating a dialysis machine, the dialysis machine generating heated air in response to being operated. The method may further include expelling the heated air from the dialysis machine by one or more internal cooling components to cool the dialysis machine. The method may further include directing the expelled heated air around one or more containers of dialysate disposed in a receptacle. The method may further include heating the dialysate by the expelled heated air.

According to various of the foregoing and other embodiments of the present disclosure, the method may further include positioning the dialysis machine on a stand of the receptacle such that the expelled heated air may be directed around the one or more containers of dialysate. The stand may position the dialysis machine vertically over a section of the receptacle for receiving the one or more containers of dialysate, and the stand may include one or more vents. The one or more vents may include baffles for directing the expelled heated air around the one or more containers of dialysate. The receptacle may be a movable cart. The one or more containers of dialysate may be stackable in the first section of the receptacle. The first section may be insulated for minimizing heat transfer from the one or more containers of dialysate to ambient air. The one or more internal cooling components may include a fan. During operation, the dialysis machine may generate internal heat resulting in heated air. The fan may be configured to simultaneously cool the dialysis machine and heat the one or more containers of dialysate by expelling the heated air from the dialysis machine and directing the expelled heated air to flow around the one or more containers of dialysate.

An exemplary embodiment of a receptacle for heating dialysate before delivery into a dialysis patient in accordance with the present disclosure may include a stand for positioning a dialysis machine, and a section for receiving one or more containers of dialysate. The one or more containers of dialysate may be positionable relative to the dialysis machine such that heated air from operating the dialysis machine may be directed around the one or more containers of dialysate to increase a temperature of the dialysate.

BRIEF DESCRIPTION OF THE DRAWINGS

By way of example, specific embodiments of the disclosed methods and devices will now be described, with reference to the accompanying drawings, in which.

DETAILED DESCRIPTION

Figure 1:
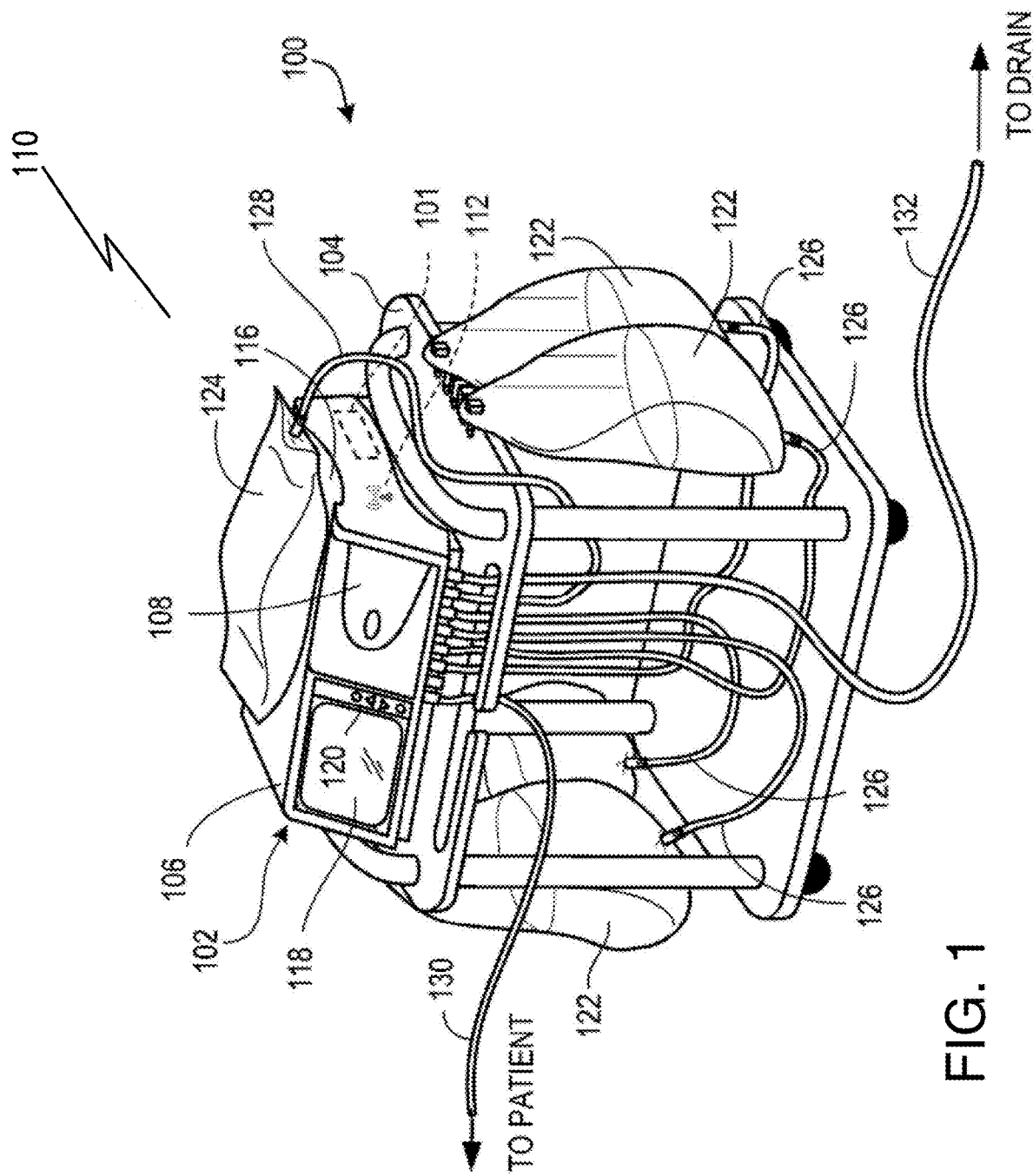
FIGS. 1 and 1A illustrate an exemplary embodiment of a dialysis machine in a dialysis system configured in accordance with the present disclosure.

The present disclosure will now be described more fully hereinafter with reference to the accompanying drawings, in which several exemplary embodiments are shown. The subject matter of the present disclosure, however, may be embodied in many different forms and types of methods and devices for dialysis machines and other potential medical devices and treatments, and should not be construed as limited to the embodiments set forth herein. Rather, these embodiments are provided so that this disclosure will be thorough and complete, and willfully convey the scope of the subject matter to those skilled in the art. In the drawings, like numbers refer to like elements throughout.

Exemplary embodiments of a dialysate heating system for dialysis machines may utilize heat generated by internal components of the dialysis machine for heating dialysate solution prior to delivery into a patient. As described above, known dialysis systems may utilize large amounts of power to heat dialysate. For example, a heater on some peritoneal dialysis machines may use up to approximately 750 Watts, when otherwise normal operation of the dialysis machine (e.g., without running the heater) may require only up to approximately 90 Watts. In some embodiments, dialysis machines may heat dialysate by batch heating, e.g., heating an entire container of dialysate (see FIGS. 1-1A). In other embodiments, dialysis machines may heat dialysate by in-line heating, e.g., continuously flowing dialysate through a warmer pouch positioned between heating elements prior to delivery into a patient (see FIG. 2).

By using heat generated by the internal components of the dialysis machine, less power may be needed to heat the dialysate prior to delivering it to the patient. In embodiments, dialysate may be stored in containers, e.g., a flexible bag, and may be formed of a Biofine™ material and/or a polyvinyl chloride (PVC) material. Although the term "bag" is used throughout, it should be understood that a dialysate bag may be any type of container capable of holding a fluid, e.g., a dialysate. In some embodiments, a fluid container may include a container in which dry concentrates are mixed with water to generate dialysate suitable for a dialysis treatment.

Figure 1A:
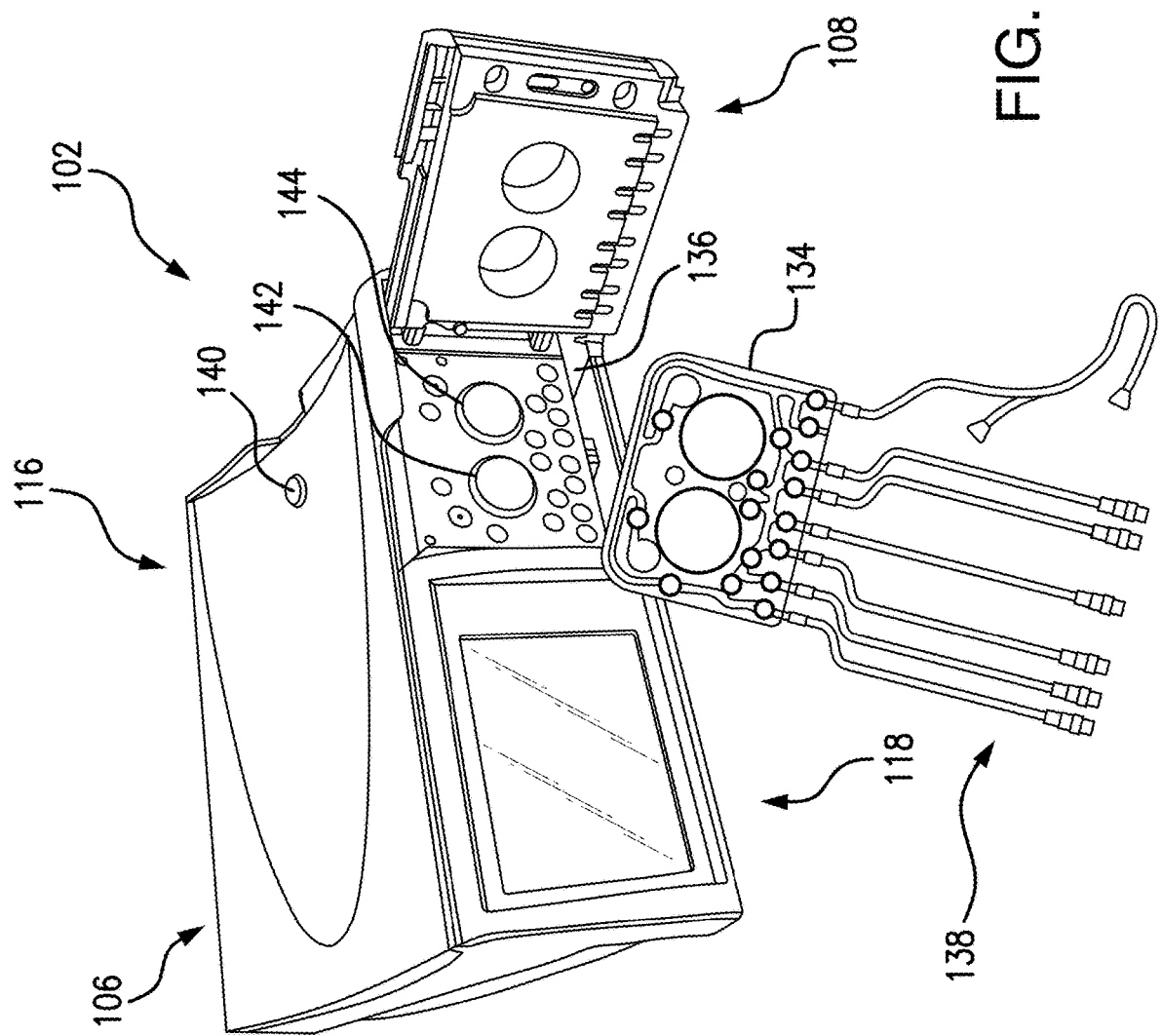

Referring now to FIGS. 1-1A, an example of a dialysis system 100 (e.g., a peritoneal dialysis (PD) system) that is configured in accordance with an exemplary embodiment of the system described herein is shown. In some implementations, the dialysis system 100 may be configured for use at a patient's home (e.g., a home PD system). The dialysis system 100 may include a dialysis machine 102 (e.g., a peritoneal dialysis machine 102, also referred to as a PD cycler) and in some embodiments the machine may be seated on a cart 104.

The dialysis machine 102 may include a housing 106, a door 108, and a cartridge interface including pump heads 142, 144 for contacting a disposable cassette, or cartridge 134, where the cartridge 134 is located within a compartment, or cavity, 136 formed between the cartridge interface and the closed door 108. Fluid lines 138 may be coupled to the cartridge 134 in a known manner, such as via a connector, and may further include valves for controlling fluid flow to and from fluid bags including fresh dialysate and warming fluid. In another embodiment, at least a portion of the fluid lines 138 may be integral to the cartridge 134. Prior to operation, a user may open the door 108 to insert a fresh cartridge 134, and to remove the used cartridge 134 after operation.

The cartridge 134 may be placed in the cavity 136 of the machine 102 for operation. During operation, dialysate fluid may be flowed into a patient's abdomen via the cartridge 134, and spent dialysate, waste, and/or excess fluid may be removed from the patient's abdomen via the cartridge 134. The door 108 may be securely closed to the machine 102. Peritoneal dialysis for a patient may include a total treatment of approximately 10 to 30 liters of fluid, where approximately 2 liters of dialysate fluid are pumped into a patient's abdomen, held for a period of time, e.g., about an hour, and then pumped out of the patient. This may be repeated until the full treatment volume is achieved, and usually occurs overnight while a patient sleeps.

A heater tray 116 may be positioned on top of the housing 106. The heater tray 116 may be any size and shape to accommodate a bag of dialysate (e.g., a 5 L bag of dialysate) for batch heating. The dialysis machine 102 may also include a user interface such as a touch screen 118 and control panel 120 operable by a user (e.g., a caregiver or a patient) to allow, for example, set up, initiation, and/or termination of a dialysis treatment. In some embodiments, the heater tray 116 may include a heating element 140, for heating the dialysate prior to delivery into the patient.

Dialysate bags 122 may be suspended from hooks on the sides of the cart 104, and a heater bag 124 may be positioned in the heater tray 116. Hanging the dialysate bags 122 may improve air management as air content may be disposed by gravity to a top portion of the dialysate bag 122. Although four dialysate bags 122 are illustrated in FIG. 1, any number of dialysate bags may be connectable to the dialysis machine 102 (e.g., 1 to 5 bags, or more), and reference made to first and second bags is not limiting to the total number of bags used in a dialysis system 100. For example, the dialysis machine may have dialysate bags 122*a*, . . . 122*n* connectable in the system 100. In some embodiments, connectors and tubing ports may connect the dialysate bags 122 and lines for transferring dialysate. Dialysate from the dialysate bags 122 may be transferred to the heater bag 124 in batches. For example, a batch of dialysate may be transferred from the dialysate bags 122 to the heater bag 124, where the dialysate is heated by the heating element 140. When the batch of dialysate has reached a predetermined temperature (e.g., approximately 98°–100° F., 37° C.), the batch of dialysate may be flowed into the patient. The dialysate bags 122 and the heater bag 124 may be connected to the cartridge 134 via dialysate bag lines or tubing 126 and a heater bag line or tubing 128, respectively. The dialysate bag lines, or tubing, 126 may be used to pass dialysate from dialysate bags 122 to the cartridge during use, and the heater bag line or tubing 128 may be used to pass dialysate back and forth between the cartridge and the heater bag 124 during use. In addition, a patient line 130 and a drain line 132 may be connected to the cartridge 134. The patient line 130 may be connected to a patient's abdomen via a catheter and may be used to pass dialysate back and forth between the cartridge and the patient's peritoneal cavity by the pump heads 142, 144 during use. The drain line 132 may be connected to a drain or drain receptacle and may be used to pass dialysate from the cartridge to the drain or drain receptacle during use.

The touch screen 118 and the control panel 120 may allow an operator to input various treatment parameters to the dialysis machine 102 and to otherwise control the dialysis machine 102. In addition, the touch screen 118 may serve as a display. The touch screen 118 may function to provide information to the patient and the operator of the dialysis system 100. For example, the touch screen 118 may display information related to a dialysis treatment to be applied to the patient, including information related to a prescription.

The dialysis machine 102 may include a processing module 101 that resides inside the dialysis machine 102, the processing module 101 being configured to communicate with the touch screen 118 and the control panel 120. The processing module 101 may be configured to receive data from the touch screen 118 the control panel 120 and sensors, e.g., weight, air, flow, temperature, and/or pressure sensors, and control the dialysis machine 102 based on the received data. For example, the processing module 101 may adjust the operating parameters of the dialysis machine 102.

The dialysis machine 102 may be configured to connect to a network 110. The connection to network 110 may be via a wired and/or wireless connection. The dialysis machine 102 may include a connection component 112 configured to facilitate the connection to the network 110. The connection component 112 may be a transceiver for wireless connections and/or other signal processor for processing signals transmitted and received over a wired connection. Other medical devices (e.g., other dialysis machines) or components may be configured to connect to the network 110 and communicate with the dialysis machine 102.

Figure 2:
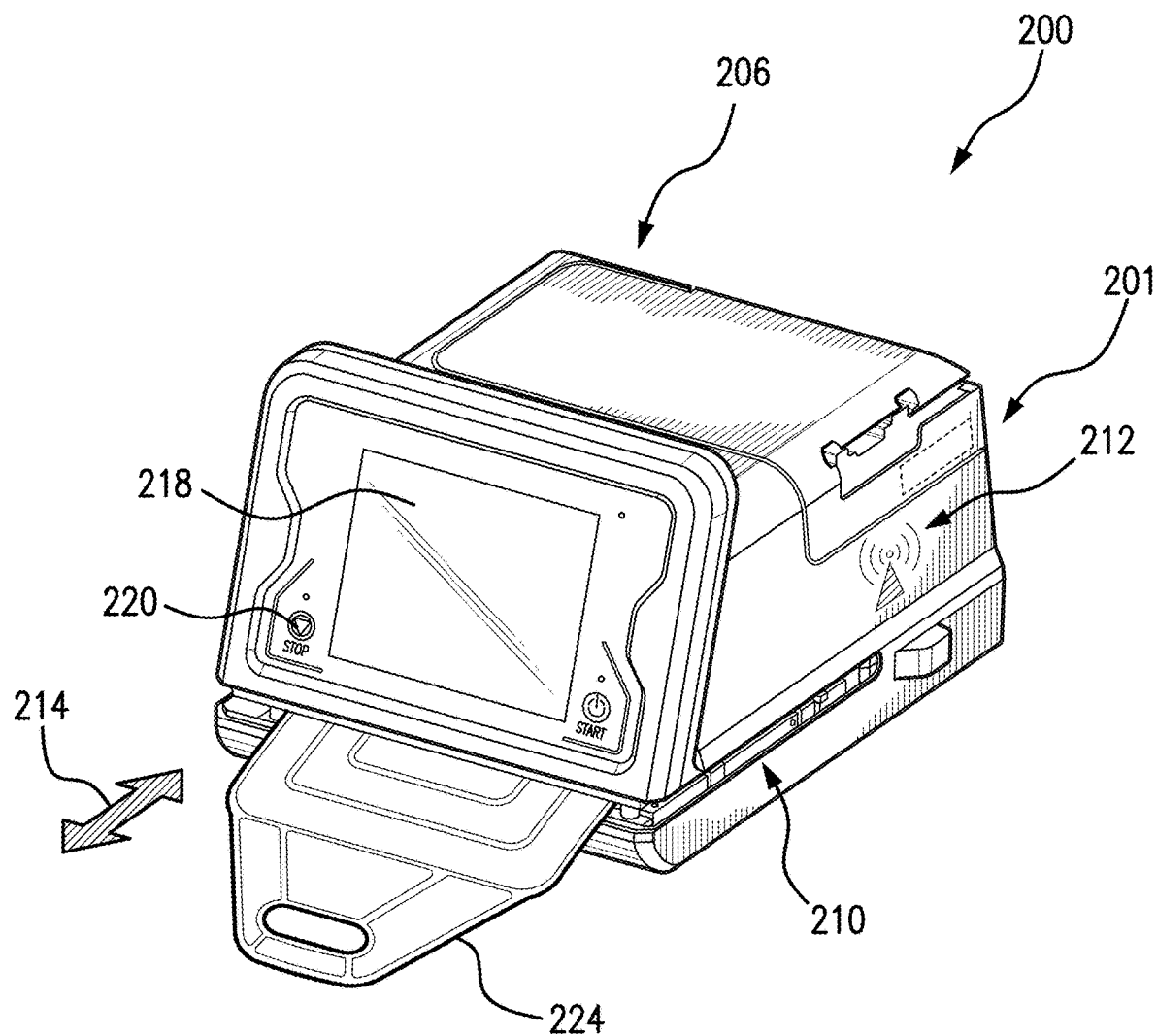
FIG. 2 illustrates another exemplary embodiment of a dialysis machine in accordance with the present disclosure.

Referring now to FIG. 2, another exemplary embodiment of a dialysis machine 200 in accordance with the present disclosure is shown. The dialysis machine 200 may be implemented in the peritoneal dialysis system 100 and may be in lieu of the dialysis machine 102, and may include, for example, a housing 206, a processing module 201, a connection component 212, a touch screen 218, and a control panel 220 operable by a user (e.g., a caregiver or a patient) to allow, for example, set up, initiation, and/or termination of a dialysis treatment. The processing module 201 and the connection component 212 may be configured similarly to the processing module 101 and connection component 112 described above. However, instead of a heater bag for batch heating being positioned on a heater tray 116 of the housing as shown in FIG. 1, one or more heating elements may be disposed internal to the dialysis machine 200. For example, a warmer pouch 224 may be insertable into an opening 210 in a direction indicated at arrow 214. It is also understood that the warmer pouch 224 may be connectable to the dialysis machine 200 via tubing, or fluid lines, via a cartridge. The tubing may be connectable so that dialysate may flow from the dialysate bags 122, through the warmer pouch 224 for heating, and to the patient.

In such in-line heating embodiments, the warmer pouch 224 may be configured so dialysate may continually flow through the warmer pouch (instead of transferred in batches for batch heating) to achieve a predetermined temperature before flowing into the patient. For example, in some embodiments the dialysate may continually flow through the warmer pouch 224 at a rate between approximately 100-300 mL/min. Internal heating elements (not shown) may be positioned above and/or below the opening 210, so that when the warmer pouch 224 is inserted into the opening 210, the one or more heating elements may affect the temperature of dialysate flowing through the warmer pouch 224. In some embodiments, the internal warmer pouch may instead be a portion of tubing in the system that is passed by, around, or otherwise configured with respect to, a heating element(s).

In some embodiments, a dialysis machine 102, 200 may provide an active measurement of the dialysate temperature in dialysate bags, heater bag, and/or the warmer pouch e.g., in the dialysate bags 122, the heater bag 124, and/or the warmer pouch 224, or combinations thereof of FIGS. 1-2. It is understood that FIGS. 1-1A illustrate that dialysate may be transferable to and stored in the heater bag 124 by "batch" until reaching an acceptable temperature for use, and that FIG. 2 illustrates dialysate continuously flowing through the warmer pouch 224 "in-line" with the dialysis machine 200, reaching an acceptable temperature by the application of internal heating elements.

Figure 3:
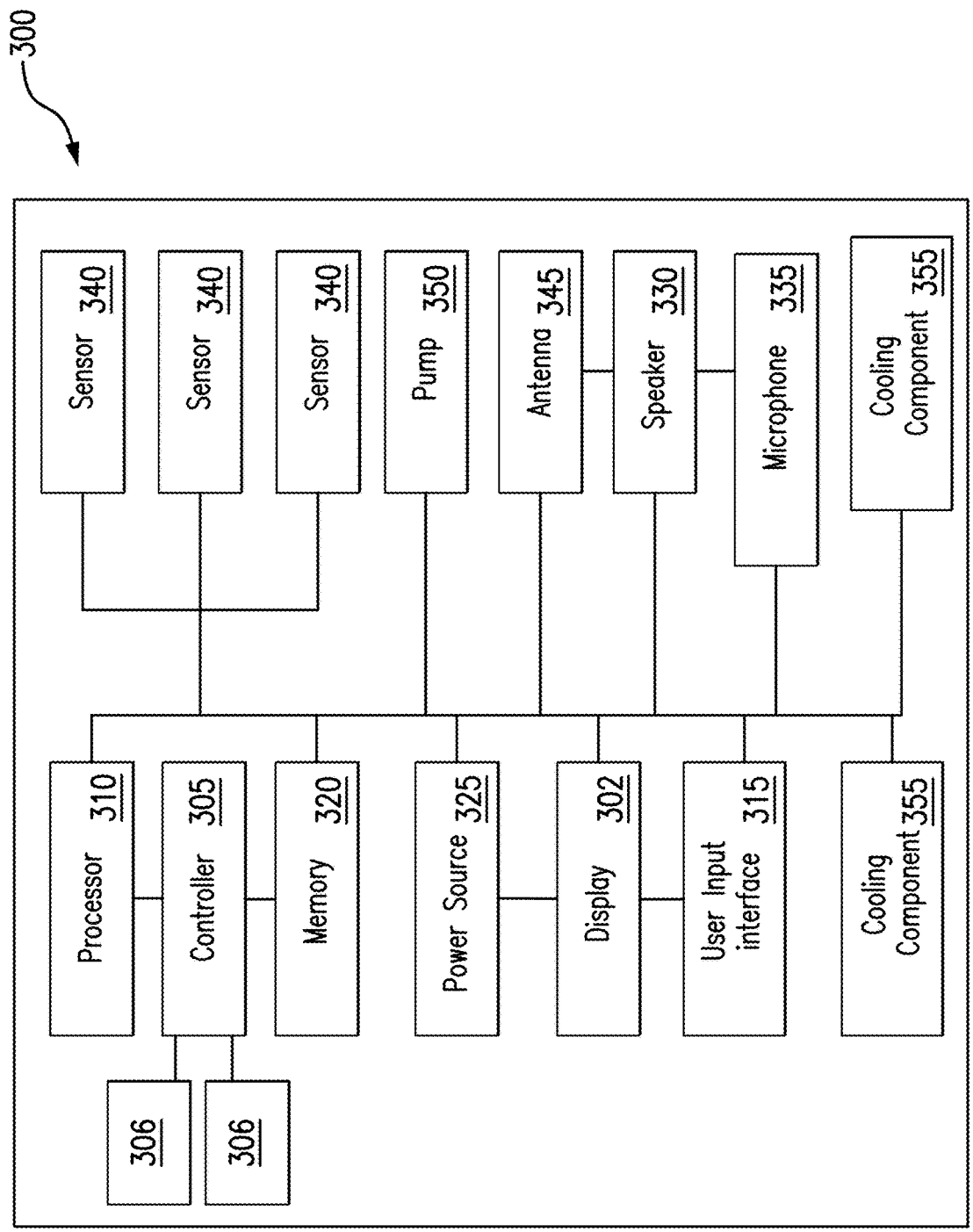
FIG. 3 is a block diagram illustrating an exemplary embodiment of a dialysis machine controller in accordance with the present disclosure.

Referring to FIG. 3, a schematic of an exemplary embodiment of a dialysis machine 300 and a controller 305 in accordance with the present disclosure are shown. The dialysis machine 300 may be a home dialysis machine, e.g., a peritoneal dialysis machine, for performing a dialysis treatment on a patient, and may be included in the system 100 for dialysis machines 102, 200, described above with respect to FIGS. 1-2. Additionally, components described with respect to the dialysis machine 300 may also be included in the dialysis machines 102, 200. It is understood that the dialysis machine 300 may be dialysis machines 102, 200, 400, and/or 515, and/or may include any or all of the features of dialysis machines 102, 200, 400, and/or 515. A power source 325 may provide power and/or a connection to an external power source to the dialysis machine 102, 200, 300. In some embodiments, one or more cooling components 355 may be disposed in the dialysis machine 102, 200, 300. As described below with respect to FIG. 4, the one or more cooling components 355 may be configured to cool internal components of the dialysis machine 102, 200, 300, including but not limited to a controller 305, processor 310, memory 320, power source 325, sensors 340, pumps 350, and the like.

The controller 305 may automatically control execution of a treatment function during a course of dialysis treatment. For example, the controller 305 may control the delivery and transfer of dialysate for dialysis machines 102, 200, 300. The controller 305 may be operatively connected to sensors 340 and deliver one or more signals to execute one or more treatment functions, or a course of treatment associated with various treatment systems. For example, dialysis treatment may include transferring dialysate from the dialysate bag 122 to the heater bag 124 and then to the patient, or delivering dialysate from the dialysate bag 122 through the warmer pouch 224 to the patient. In some embodiments, a timer may be included for timing triggering of sensors 340. It is understood that sensors, including but not limited to pressure sensors, weight sensors, flow sensors, air sensors, and temperature sensors, may detect dialysate temperature, fluid volume, fluid flow rate, and fluid flow pressure for the dialysis machine 102, 200, 300 to determine flow delivery to and from the patient. For example, the dialysis machine 102, 200, 300 may include a plurality of sensors for detection and/or measurement of any combination of temperature, pressure, volume, fluid flow. Multiple sensors may also be included to detect and/or measure individually the temperature, pressure, volume, fluid flow. Although FIG. 3 illustrates the components integral to the dialysis machine 300, at least one of the controller 305, processor 310, and/or memory 320 may be configured to be external and wired or wirelessly connected to the dialysis machine 102, 200, 300, as an individual component of a dialysis system. In some embodiments the controller 305, processor 310 and memory 320 may be remote to the dialysis machine and configured to communicate wirelessly.

In some embodiments, the controller 305, processor 310, and/or memory 320 of the dialysis machine 300 may receive sensor 340 signals indicating complete dialysate transfer of the dialysate bags, and indicating process parameters, such as temperature, pressure, volume, flow rate, and the like. For example, each dialysate bag (e.g., the dialysate bags 122 and the heater bag 124) may contain an approximate amount of dialysate, such that "approximate amount" may be defined as a 3 L dialysate bag containing 3000 to 3150 mL, a 5 L dialysate bag containing 5000 to 5250 mL, and a 6 L dialysate bag containing 6000 to 6300 mL. Although bag volume is described herein as 3 L, 5 L and 6 L, it is understood that the specified volumes are only exemplary and bag volume may be any volume, and an "approximate" volume may be in a range within 10% of the desired volume. The controller 305 may also detect connection of all dialysate bags 122 connected. The controller 305 may monitor the dialysate bags 122 for dialysate transfer, so that the controller 305 knows the volume of dialysate that has been transferred from each dialysate bag 122.

Communication between the controller 305 and the treatment system may be bi-directional, whereby the treatment system acknowledges control signals, and/or may provide state information associated with the treatment system and/ or requested operations. For example, system state information may include a state associated with specific operations to be executed by the treatment system (e.g., trigger pump to deliver dialysate, trigger pumps and/or compressors to deliver filtered blood, and the like) and a status associated with specific operations (e.g., ready to execute, executing, completed, successfully completed, queued for execution, waiting for control signal, and the like). In some embodiments, the dialysis machine 102, 200, 300, 400, 515 may be operably connected through a network to other system components, for coordinated care, across one or more healthcare providers.

In embodiments, the dialysis machine 102, 200, 300 may include at least one pump 350 operatively connected to the controller 305. During a treatment operation, the controller 305 may control the pump 350 for pumping fluid, e.g., fresh and spent dialysate, to and from a patient. The pump 350 may also pump dialysate from the dialysate bag 122 to the heater bag 124, or to another dialysate bag 122. In embodiments where the warmer pouch 224 is in-line with the dialysis machine 200, the pump 350 may pump the dialysate through the warmer pouch 224 directly to the patient. The controller 305 may also be operatively connected to a speaker 330 and a microphone 335 disposed in the dialysis machine 300. A user input interface 315 may include a combination of hardware and software components that allow the controller 305 to communicate with an external entity, such as a patient or other user, and a display 302 may display information to the user or medical professional. These components may be configured to receive information from actions such as physical movement or gestures and verbal intonation. In embodiments, the components of the user input interface 315 may provide information to external entities. Examples of the components that may be employed within the user input interface 315 include keypads, buttons, microphones, touch screens, gesture recognition devices, display screens, and speakers. The dialysis machine 102, 200, 300 may also be wirelessly connectable via the antenna 345 for remote communication.

As shown in FIG. 3, sensors 340 may be included for monitoring one or more parameters and may be operatively connected to at least the controller 305, processor 310, and memory 320. The processor 310 may be configured to execute an operating system, which may provide platform services to application software, e.g., for operating the dialysis machine 300. These platform services may include inter-process and network communication, file system management and standard database manipulation. One or more of many operating systems may be used, and examples are not limited to any particular operating system or operating system characteristic. In some examples, the processor 310 may be configured to execute a real-time operating system (RTOS), such as RT/Linux, or a non-real time operating system, such as BSD or GNU/Linux.

According to a variety of examples, the processor 310 may be a commercially available processor such as a processor manufactured by INTEL, AMD, MOTOROLA, and FREESCALE. However, the processor 310 may be any type of processor, multiprocessor or controller, whether commercially available or specially manufactured. For instance, according to one example, the processor 310 may include an MPC823 microprocessor manufactured by MOTOROLA.

The memory 320 may include a computer readable and writeable nonvolatile data storage medium configured to store non-transitory instructions and data. In addition, the memory 320 may include a processor memory that stores data during operation of the processor 310. In some examples, the processor memory includes a relatively high performance, volatile, random access memory such as dynamic random access memory (DRAM), static memory (SRAM), or synchronous DRAM. However, the processor memory may include any device for storing data, such as a non-volatile memory, with sufficient throughput and storage capacity to support the functions described herein. Further, examples are not limited to a particular memory, memory system, or data storage system.

The instructions stored on the memory 320 may include executable programs or other code that may be executed by the processor 310. The instructions may be persistently stored as encoded signals, and the instructions may cause the processor 310 to perform the functions described herein. The memory 320 may include information that is recorded, on or in, the medium, and this information may be processed by the processor 310 during execution of instructions. The memory 320 may also include, for example, specification of data records for user timing requirements, timing for treatment and/or operations, and historic sensor information. The medium may, for example, be optical disk, magnetic disk or flash memory, among others, and may be permanently affixed to, or removable from, the controller 305.

A pressure sensor may be included for monitoring fluid pressure of the dialysis machine 102, 200, 300, although the sensors 340 may also include any of a heart rate sensor, a respiration sensor, a temperature sensor, a flow sensor, a weight sensor, a video sensor, an air sensor, an air bubble sensor, a thermal imaging sensor, an electroencephalogram sensor, a motion sensor, audio sensor, an accelerometer, or capacitance sensor. It is appreciated that the sensors 340 may include sensors with varying sampling rates, including wireless sensors.

The controller 305 may be disposed in the dialysis machine 102, 200, 300 or may be coupled to the dialysis machine 102, 200, 300 via a communication port or wireless communication links, shown schematically as communication element 306 (see FIG. 3). According to various examples, the communication element 306 may support a variety of one or more standards and protocols, examples of which include USB, WiFi, TCP/IP, Ethernet, Bluetooth, Zigbee, CAN-bus, IP, IPV6, UDP, UTN, HTTP, HTTPS, FTP, SNMP, CDMA, NMEA and/or GSM. As a component disposed within the dialysis machine 300, the controller 305 may be operatively connected to any one or more of the sensors 340, pump 350, or combinations thereof. The controller 305 may communicate control signals or triggering voltages to the components of the dialysis machine 102, 200, 300. As discussed, exemplary embodiments of the controller 305 may include wireless communication interfaces. The controller 305 may detect remote devices to determine if any remote sensors are available to augment any sensor data being used to evaluate the patient.

Figure 4:
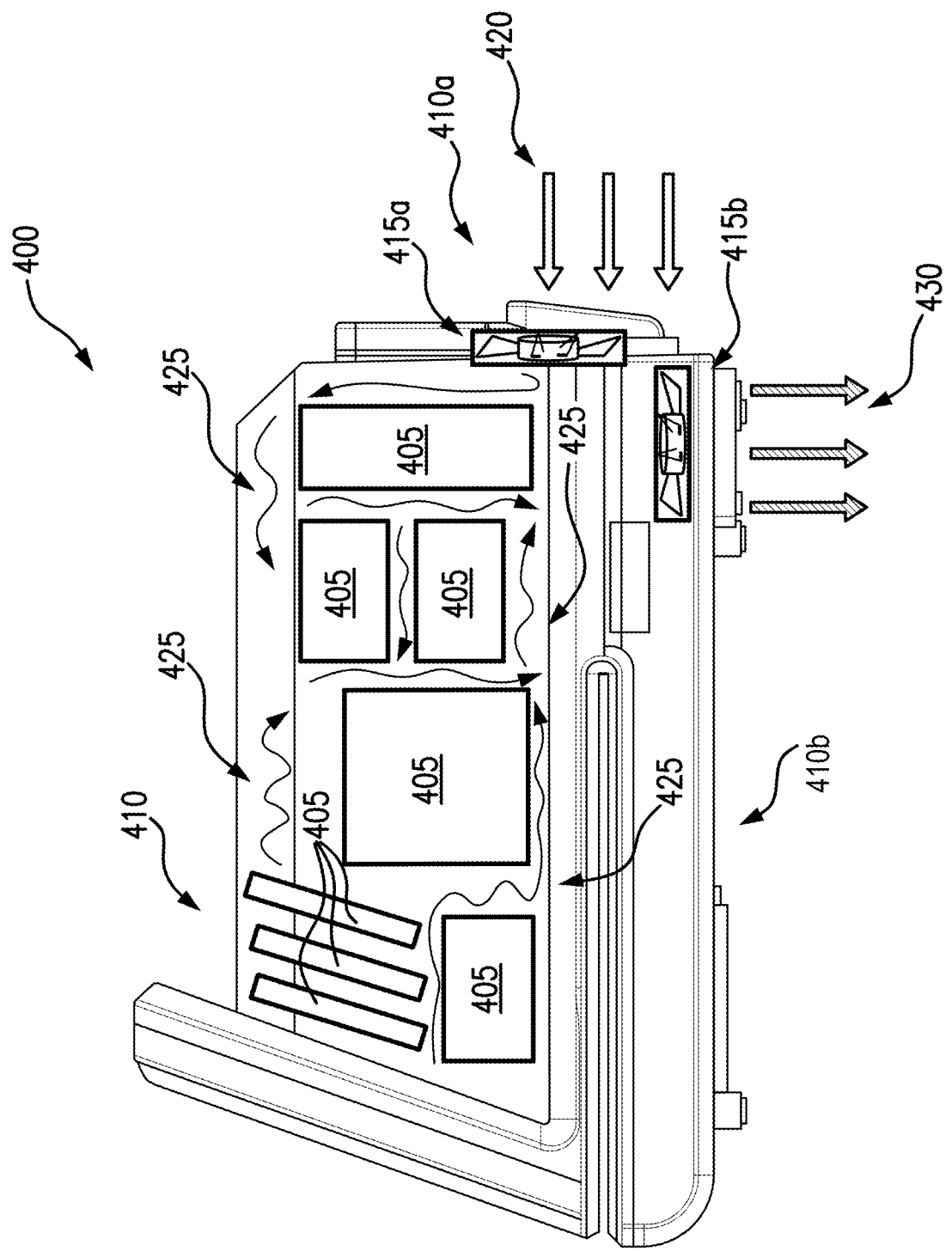
FIG. 4 illustrates an exemplary embodiment of a fluid flow path of a dialysis machine in accordance with the present disclosure.

Referring now to FIG. 4, a sectional view illustrating an exemplary embodiment of a dialysis machine 400 in accordance with the present disclosure is shown. It is understood that the dialysis machine 400 may be dialysis machines 102, 200, 300, and/or 515, and/or may include any or all of the features of dialysis machines 102, 200, 300, and/or 515. As shown, a plurality of components 405 may be disposed in a housing 410 of the dialysis machine 400, which may include any of a controller, processor, memory, sensors, pumps, power source, or combinations thereof, as well as other components. For example, the components 405 may be internal components, e.g., to the dialysis machines 102, 200, 300, 400 and/or 515. Operation of these components 405 may generate heat, which may need to be expelled from the housing 410 of the dialysis machine 400. It may be advantageous to expel the generated heat to minimize and/or prevent overheating of the components 405.

In some embodiments, a first cooling component 415a may be disposed on the housing 410 to allow a fluid, e.g., air or other cooling gas, to flow into the housing 410. In some embodiments, the first cooling component 415a may be a fan, which may be configured to operate by drawing air or other cooling gas into the housing 410 of the machine 400, e.g., as shown by arrows 420. In embodiments, the air or other cooling gas drawn in by the first cooling component 415a may be at room temperature, or approximately 73° F. (23° C.). The first cooling component 415a may be disposed in the housing in any location to maximize air intake. In some embodiments, the first cooling component 415a may be disposed in a rear face 410a of the housing 410. In other embodiments, the first cooling component 415a may be disposed in any surface of the housing to maximize air intake, including but not limited to a top, sides, and/or bottom face. In some embodiments, the first cooling component 415a may be a hose connected to a gas supply, e.g., air or other cooling gas, for feeding into the dialysis machine 400.

When the air has been drawn into the housing 410, it may flow around the plurality of components 405, e.g., as shown in flow paths 425. Heat generated during operation may emanate from the plurality of components 405, resulting in heated air adjacent the components 405. One or more airflow paths 425 may flow the heated air around the plurality of components 405, so that heated air flows out of the housing 410, e.g., is expelled, by a second cooling component 415b, e.g., as shown by arrows 430. For example, the second cooling component may include a fan configured to operate by expelling the heated air out of the housing 410. In some embodiments, the expelled heated air may be at a temperature approximately between 73° F. (23° C.) and 99° F. (37° C.), as the dialysis machine 400 becomes heated during operation (see e.g., FIG. 6). The second cooling component 415b may be disposed in the housing 410 of the dialysis machine 400 to direct the expelled heated air around the containers of dialysate, e.g., dialysate bags (see FIGS. 5A-5B). For example, the second cooling component 415b may be disposed on a bottom surface 410b of the housing 410.

The expelled heated air may flow vertically downward, with the containers of dialysate being positioned vertically below (e.g., the dialysis machine 400 is positioned vertically over the containers of dialysate) for the expelled heated air to flow around the dialysate bags. In other embodiments, the second cooling component 415b may be disposed on any surface of the housing 410 to best direct the expelled heated air to the dialysate bags, including but not limited to the rear, sides, and/or top faces. In some embodiments, the second cooling component 415b may include an opening including vents, for directing the expelled heated air over the dialysate bags.

A first cooling component 415a configured to draw cool air or other cooling gas into the housing 410, in combination with a second cooling component 415b configured to expel heated air out of the housing 410, may result in a fluid flow path to ensure the components 405 are sufficiently cooled during operation. Although a first and second cooling components 415a, 415b are illustrated in FIG. 4, it is understood that any number of cooling components may be included in the housing 410 of the dialysis machine 400.

Figure 5A:
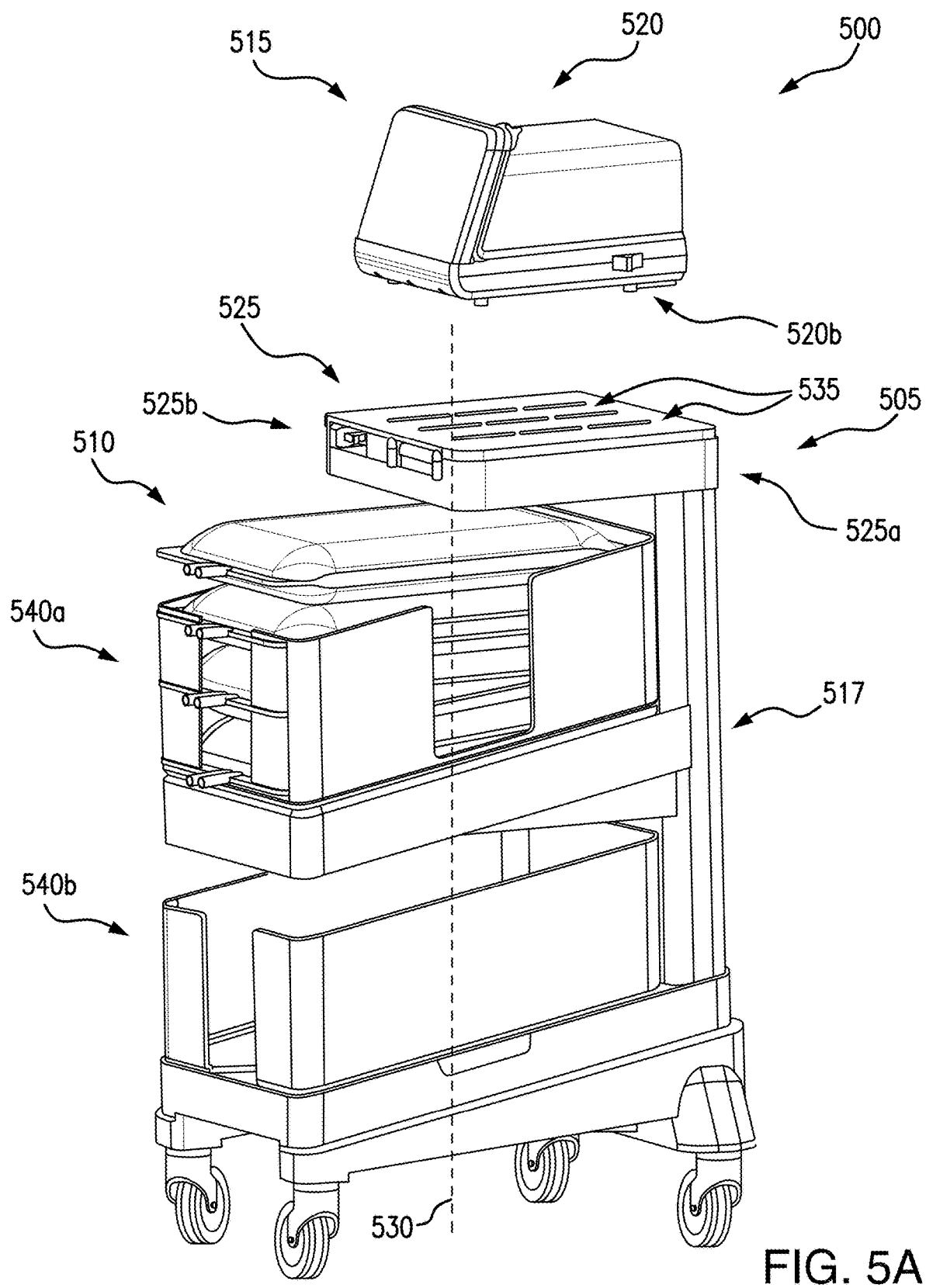
FIGS. 5A-5B illustrate an exemplary embodiment of a receptacle in accordance with the present disclosure.
Figure 5B:
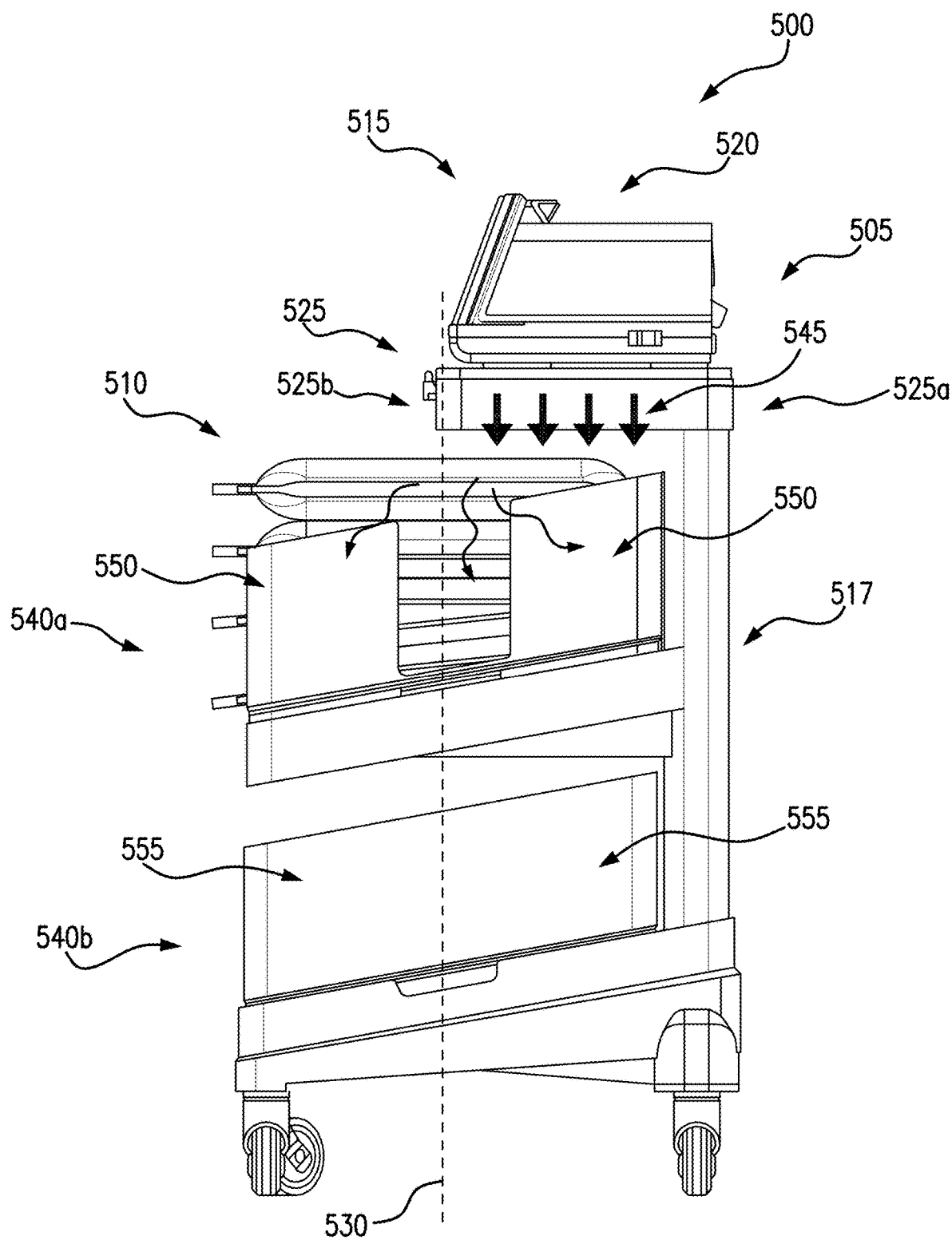

According to exemplary embodiments of the present disclosure, the expelled heated air may be utilized to at least partially heat one or more containers of dialysate, e.g., dialysate bags 122 (see FIGS. 5A-5B). As described above, a large amount of power may be needed to heat the dialysate to body temperature in a conventional manner, which may be disadvantageous for operating a dialysis machine in areas having limited power generation (e.g., developing countries, field operations, and/or rural environments).

In some embodiments, the expelled heated air may be directed to flow over the dialysate bags to convectively warm the dialysate, thereby requiring less power to heat the dialysate when it is drawn to the system prior to delivery to the patient. For example, a peritoneal dialysis treatment may deliver ten liters of dialysate to the patient, with five fills of two liters each, over eight hours. Although dialysate may be heated by heaters at least initially during a dialysis treatment, dialysate temperature may be increased throughout the treatment by heating with expelled heated air. For example, as the dialysis treatment progresses, the dialysate may be pre-heated by the expelled heated air, thereby requiring less power to heat the dialysate to the desired body temperature (e.g., 99° F. (37° C.)).

It is understood that convective heat transfer may be calculated by the following equation:

$$\frac{Tf - Tair}{Ti - Tair} = e^{-\left[\frac{hA}{\rho cV}\right]t} \qquad \text{Eq. 1}$$

Where Tf is the final temperature of the dialysate bags, Ti is the initial temperature of the dialysate bags, e.g., room temperature (approximately 73° F. (23° C.)), and Tair is the temperature of the expelled heated air, e.g., 37° C. Additionally, h may be the convection coefficient, or 10 W/m²C, and A may be the surface area of the dialysate bags. Additionally, p may the solution density, or 997 kg/m³, c may be the solution specific heat, or 4.18 kJ/kgc, and V may be the volume of the dialysate. t may be the time, e.g., the time during a dialysis treatment.

In some embodiments, the dialysate bags may be a flexible container, and may be substantially rectangular in shape. The dialysate bags may be vertically stacked together, such as described below with respect to FIGS. 5A-5B. A volume V may be calculated by multiplying the total dialysate bag length (1) times width (w) times height (h). For example, a length of the dialysate bags may be approximately 0.2-0.7 m, and in some embodiments may be 0.4 m. A width of the dialysate bags may be approximately 0.05-0.4 m, and in some embodiments may be 0.25 m. A height of the dialysate bags, e.g., vertically stacked together, may be approximately 0.05-0.2 m, and in some embodiments may be 0.1 m. An initial volume V may therefore be 0.4×0.25×0.1=0.01 m³, or 10 L. It is understood that the height of the dialysate bags may change during a dialysis treatment, and that the initial height may be 0.1 m (e.g., when the dialysate bags are full), and an initial volume V may be 0.01 m³, or 10 L. For example, the bags may be depleted of dialysate as the dialysate is delivered to the patient for treatment. A surface area A of the total dialysate bags may be calculated by the formula A=(width×length)+2(length×height)+2(height×width), or (0.4×0.25)+2(0.4×0.1)+2(0.25×0.1)=0.2311¹² as an initial surface area (e.g., when the dialysate bags are full). In embodiments, a bottom surface of the dialysate bags may not be exposed to convective air cooling, such that only the top surface is included in the calculation.

When the variables are substituted in Eq. 1, the final temperature Tf may be calculated as follows:

$$37 - 14e^{-\left[\frac{hA}{\rho cV}\right]t} \qquad \text{Eq. 2}$$

Figure 6:
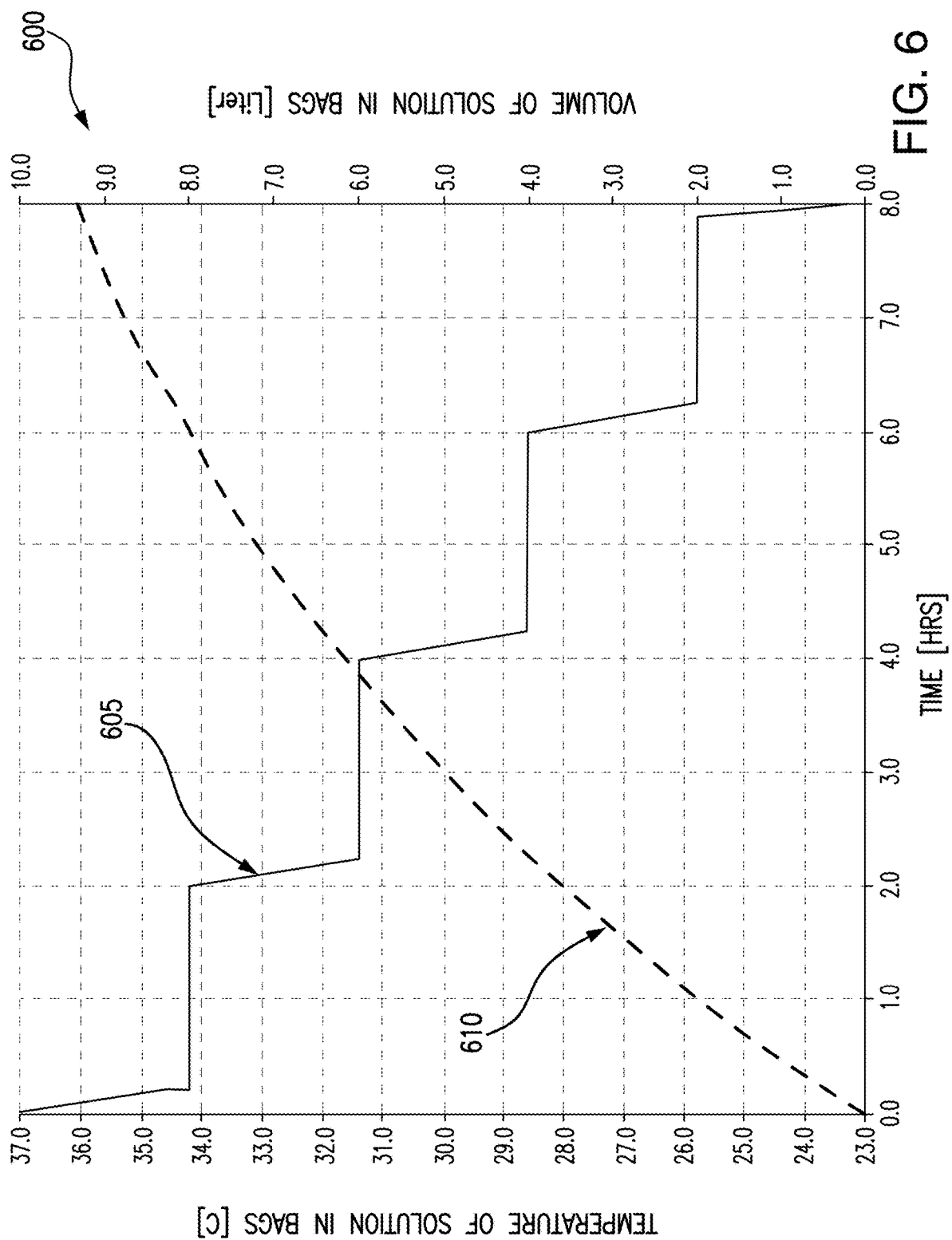
FIG. 6 illustrates an exemplary charting of dialysate temperature during a dialysis treatment cycle in accordance with the present disclosure.

As the time of the treatment changes, the final temperature Tf of the dialysate bags may change, as shown in the chart of FIG. 6. As shown in the chart 600, a peritoneal dialysis treatment may last for approximately 8 hours, as fresh dialysate is delivered to the patient, and used dialysate and waste is removed from the patient in cycles, as described above. Reference numeral 605 indicates the change in volume of dialysate during a dialysis treatment, which decreases by 2 liters every two hours. Reference numeral 610 indicates the temperature in the dialysate bags, e.g., final temperature Tf (° C.) during the dialysis treatment. For example, at the beginning of the dialysis treatment (t=0), the dialysate bags may be at room temperature, or 23° C. By directing the expelled heated air to flow around the dialysate bags as described above, the temperature of the dialysate bags may increase during the treatment. For example, at t=2 hours, the dialysate bags may be 28° C., at t=4 hours, the dialysate bags may be 31.5° C., and at t=6 hours, the dialysate bags may be 34° C.

By raising the temperature of the dialysate by approximately 10 degrees prior to delivery to the heater bag 124 for batch heating (see FIG. 1), and/or flowing through the warmer pouch 224 for in-line heating (see FIG. 2), less demand on the heating elements may be needed. For example, less power may be needed by the heating elements to heat the dialysate from 31.5° C. (t=4 hours) to 37° C. when the expelled heated air is directed to flow around the dialysate bags, as opposed to heating the dialysate from room temperature (23° C.).

In embodiments, the dialysate bags may be vertically stacked and positioned relative to the dialysis machine so that expelled heated air may be directed over the dialysate bags. In some embodiments, a receptacle may be used to position the dialysate bags relative to the dialysis machine. Referring now to FIGS. 5A-5B, an exemplary embodiment of a dialysis system 500 in accordance with the present disclosure is shown. For clarity, tubing connections are not illustrated.

In embodiments, a receptacle 505 may be configured to receive one or more containers of dialysate 510 (e.g., dialysate bags). The one or more containers of dialysate 510 may be positionable relative to the expelled heated air of the dialysis machine 515 as described above. Although four dialysate bags are illustrated in FIGS. 5A-5B, it is understood that the one or more containers of dialysate 510 may be any number of dialysate bags needed for a patient to receive a full dialysis treatment. It is also understood that in some embodiments the dialysate bags may be the same size and/or shape, and in other embodiments the dialysate bags may be differently sized and/or shaped. In some embodiments, the receptacle 505 may be a cart, e.g., a movable cart. For example, the second cooling component may expel heated air out of a bottom surface 520*b* of a housing 520 of the dialysis machine 515 so that the expelled heated air may be directed to the dialysate bags 510. The expelled heated air may be flowable around the one or more containers of dialysate 510 to increase a temperature of the dialysate as described above (see FIGS. 4 and 6). It is understood that the dialysis machine 515 may be dialysis machines 102, 200, 300, 400, and/or may include any or all of the features described in the dialysis machines 102, 200, 300, 400.

In some embodiments, the receptacle 505 may include a stand 525 for positioning the dialysis machine 515, e.g., so that the expelled heated air may be directed around the one or more containers of dialysate 510. For example, the stand 525 may position the dialysis machine 515 vertically (e.g., along axis 530) over the one or more containers of dialysate 510. The stand 525 may be coupled to the receptacle 505, for example, coupled to a post 517, and may be any shape and size to receive the dialysis machine 515. In some embodiments, the stand 525 may be substantially rectangular and may be substantially flat (e.g., tray, disk, and/or plate). The post 517 may extend in a direction parallel to axis 530, e.g., vertically. The stand 525 may be coupled to a top section of the post 517, and may be coupled at a first end of the stand 525*a*, a second end of the stand 525*b* being unconstrained. For example, the stand 525 may extend in a direction substantially perpendicular to the axis 530 and at least partially over the one or more containers of dialysate 510. When the dialysis machine 515 is positioned on the stand 525, it may also be vertically over the dialysate bags.

The stand 525 may include one or more vents 535 for directing the expelled heated air around the containers of dialysate 510. In some embodiments, the vents 535 may be thru-holes on the stand, to provide openings for the expelled heated air to flow through to the one or more containers of dialysate 510. In other embodiments, the vents 535 may be configured to direct the expelled heated air evenly around the one or more containers of dialysate 510. For example, heated air may be expelled from the housing 520 of the dialysis machine 515 at a single location by the second cooling component. The vents 535 may be configured to flow the expelled heated air through the stand 525 to heat the dialysate bags evenly. For example, FIG. 5B shows arrows indicated at reference numeral 545 distributing the expelled heated air across the entire stand 525 to flow around the dialysate bags, as opposed to only at the second cooling component.

In some embodiments, the vents 535 may include baffles, or flaps (not shown), which may be manually and/or automatically adjustable to adjust the flow of the expelled heated air as desired. For example, adjustable baffles may be advantageous to adjust a flow of the expelled heated air to differently sized and/or shaped dialysate bags.

The receptacle 505 may further include a first section 540a and/or a second section 540b. In some embodiments, the first section 540a may be configured to receive the one or more containers of dialysate 510, e.g., the dialysate bags. For example, the dialysate bags may be vertically stackable (e.g., along the axis 530) in the first section 540a. The first section 540a may be vertically below the stand 525 along the axis 530. In embodiments, the first section 540a may be a tray, a bin, or other type of enclosure, partial or full, to receive and retain the one or more containers of dialysate 510. For example, as shown in FIGS. 5A-5B, the dialysate bags 510 may be retained in a partially enclosed first section 540a, having sides 550 extending around, e.g., about axis 530, and a perimeter of the dialysate bags. The sides 550 extend vertically along the axis 530, so that dialysate bags stacked together may be held in a stacked position. In some embodiments, the first section 540a may be substantially rectangular, or box-shaped, and/or any size and/or shape configured to receive the dialysate bags.

In some embodiments, the first section 540a may be insulated for minimizing heat transfer from the one or more containers of dialysate to ambient air. For example, the sides 550 may be formed of an insulating material, including but not limited to plastic, composite, and/or multi-layers. In some embodiments, the sides 550 may fully enclose the dialysate bags, and may include a top portion (not shown) to encapsulate the dialysate bags. It may be advantageous to insulate the dialysate bags from ambient air so that when the dialysate is heated by the expelled heated air from the dialysis machine 515, the dialysate may better retain the heat and may increase in temperature a rate higher than when the dialysate bags are exposed to ambient air.

In some embodiments, the receptacle 505 may further include a second section 540b, for retaining additional dialysate bags, and/or other storage. In some embodiments, the second section 540b may be configured so that expelled heated air may be directed to the second section 540b to heat one or more containers of dialysate 510. The second section 540b may be configured similarly to the first section 540a, for example, being formed substantially rectangular about the axis 530, and having vertical sides 555 extending along the axis 530. The second section 540b may be configured to receive and/or retain one or more containers of dialysate 510, e.g., a stack of dialysate bags.

As described above with respect to FIG. 4, during operation the dialysis machine may generate internal heat by a plurality of internal components. This heated air may be expelled by one or more cooling components, e.g., an intake fan and/or an exhaust fan. The fans may be configured to simultaneously cool the plurality of internal components by drawing in cool air (e.g., room temperature) and/or expelling the air heated by the operation of the internal dialysis machine components. The expelled heated air 545 may be directed to the dialysate bags by the vents 535 in the stand 525, to the first section 540a so that the containers of dialysate 510 may be heated by the expelled heated air. For example, the expelled heated air 545 may flow around the dialysate bags, e.g., a top surface of a dialysate bag on top of the stacked dialysate bags, and/or around the sides of the dialysate bags, in spaces between the sides 550, as shown by arrows 560. By raising the temperature of the dialysate by the expelled heated air, even partially (see FIG. 6), the dialysis system may conserve power during a dialysis treatment. For example, the dialysis system may conserve heating energy because the heating elements may be driven to overcome a smaller temperature range (e.g., 31.5° C. to 37° C. at t=4 hours) as opposed to heating dialysate from room temperature (e.g., 23° C. to 37° C.).

In embodiments, the dialysate temperature in the containers of dialysate 510 may be monitored by the dialysis machine 102, 200, 300, 400, 515 as the dialysate flows through the tubing into the heater bag 124 and/or the warmer pouch 224. In some embodiments, the dialysate bags may have temperature sensors, which may be wired and/or wirelessly connected to the dialysis machine for tracking and monitoring the dialysate temperature. In some embodiments, the dialysis machine may include a vent control system. A vent control system may receive data from one or more temperature sensors positioned on dialysate bags, and may automatically open, close, and/or redirect vents in response to a detected temperature exceeding a predetermined maximum temperature and/or falling below a predetermined minimum temperature.

Some embodiments of the disclosed systems may be implemented, for example, using a storage medium, a computer-readable medium or an article of manufacture which may store an instruction or a set of instructions that, if executed by a machine (i.e., processor or microcontroller), may cause the machine to perform a method and/or operations in accordance with embodiments of the disclosure. In addition, a server or database server may include machine readable media configured to store machine executable program instructions. Such a machine may include, for example, any suitable processing platform, computing platform, computing device, processing device, computing system, processing system, computer, processor, or the like, and may be implemented using any suitable combination of hardware, software, firmware, or a combination thereof and utilized in systems, subsystems, components, or sub-components thereof. The computer-readable medium or article may include, for example, any suitable type of memory unit, memory device, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

As used herein, an element or operation recited in the singular and proceeded with the word "a" or "an" should be understood as not excluding plural elements or operations, unless such exclusion is explicitly recited. Furthermore, references to "one embodiment" of the present disclosure are not intended to be interpreted as excluding the existence of additional embodiments that also incorporate the recited features.

To the extent used in this description and in the claims, a recitation in the general form of "at least one of [a] and [b]" should be construed as disjunctive. For example, a recitation of "at least one of [a], [b], and [c]" would include [a] alone, [b] alone, [c] alone, or any combination of [a], [b], and [c].

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A system for heating dialysate before delivery into a dialysis patient, comprising:
    a dialysis machine including one or more internal cooling components configured to expel heated air from the dialysis machine; and
    a receptacle configured to receive one or more containers of dialysate, the one or more containers of dialysate being positionable relative to the expelled heated air of the dialysis machine, wherein the expelled heated air is flowable around the one or more containers of dialysate to increase a temperature of the dialysate;
    wherein the receptacle includes:
        a stand arranged and configured to position the dialysis machine thereon, the stand including one or more vents; and
        a section arranged and configured to receive the one or more containers of dialysate therein, the section positioned below the stand and the one or more vents so that the expelled heated air is directed out of the dialysis machines through the one or more vents formed in the stand and into the section of the receptacle and around the one or more containers of dialysate.

2. The system according to claim 1, wherein the one or more vents includes baffles for directing the expelled heated air around the one or more containers of dialysate.

3. The system according to claim 1, wherein the receptacle is a movable cart.

4. The system according to claim 1, wherein the one or more containers of dialysate are stackable in the section of the receptacle.

5. The system according to claim 4, wherein the section is insulated for minimizing heat transfer from the one or more containers of dialysate to ambient air.

6. The system according to claim 1, wherein the one or more internal cooling components includes a fan.

7. The system according to claim 6, wherein during operation the dialysis machine generates internal heat resulting in heated air, wherein the fan is configured to simultaneously cool the dialysis machine and heat the one or more containers of dialysate by expelling the heated air from the dialysis machine and directing the expelled heated air to flow around the one or more containers of dialysate.

8. A method for heating dialysate before delivery into a dialysis patient, comprising:
    operating a dialysis machine, the dialysis machine generating heated air in response to being operated;
    expelling the heated air from the dialysis machine by one or more internal cooling components to cool the dialysis machine;
    directing the expelled heated air around one or more containers of dialysate disposed in a receptacle; and
    heating the dialysate by the expelled heated air;
    wherein the dialysis machine is positioned on a stand of the receptacle and the one or more containers of dialysate are positioned in a first section of the receptacle, the first section being insulated for minimizing heat transfer from the one or more containers of dialysate to ambient air.

9. The method according to claim 8, wherein the stand positions the dialysis machine vertically over the first section of the receptacle, the stand including one or more vents.

10. The method according to claim 9, wherein the one or more vents includes baffles for directing the expelled heated air around the one or more containers of dialysate.

11. The method according to claim 8, wherein the receptacle is a movable cart.

12. The method according to claim 9, wherein the one or more containers of dialysate are stackable in the first section of the receptacle.

13. The method according to claim 8, wherein the one or more internal cooling components includes a fan.

14. The method according to claim 13, wherein during operation the dialysis machine generates internal heat resulting in heated air, wherein the fan is configured to simultaneously cool the dialysis machine and heat the one or more containers of dialysate by expelling the heated air from the dialysis machine and directing the expelled heated air to flow around the one or more containers of dialysate.

* * * * *